United States Patent [19]

Pascaloff

[11] Patent Number: 5,122,142
[45] Date of Patent: Jun. 16, 1992

[54] IRRIGATING SAW BLADE

[75] Inventor: John H. Pascaloff, Goleta, Calif.

[73] Assignee: Hall Surgical Division of Zimmer, Inc., Carpinteria, Calif.

[21] Appl. No.: 581,935

[22] Filed: Sep. 13, 1990

[51] Int. Cl.⁵ .............................................. A61B 17/14
[52] U.S. Cl. ...................................... 606/82; 606/79; 606/171; 606/178
[58] Field of Search ....................... 606/53, 82, 84, 79, 606/171, 176, 177, 178, 179; 30/123.3, 123.4, 166.3

[56] References Cited

U.S. PATENT DOCUMENTS

| | | | |
|---|---|---|---|
| H571 | 2/1989 | Hollinger et al. | |
| 4,008,720 | 2/1977 | Brinkmann et al. | 606/178 X |
| 4,513,742 | 4/1985 | Arnegger | 606/178 |
| 4,667,408 | 5/1987 | Kirk | 30/123.3 |

*Primary Examiner*—Robert A. Hafer
*Assistant Examiner*—Brian E. Hanlon
*Attorney, Agent, or Firm*—Todd A. Dawson

[57] ABSTRACT

The surgical saw blade includes a main body portion and a cover portion joined to provide an enclosed manifold space. Irrigation channels extend from the manifold space to saw teeth provided on the saw blade. In one embodiment of the invention the saw teeth are provided at an end portion of the saw blade. In another embodiment of the invention the irrigation channels extend toward saw teeth provided along the longitudinal side edge of the saw blade. In either embodiment of the invention the irrigation channels commonly communicate with the fluid manifold and are uniformly distributed among the cutting teeth to provide a uniform distribution of fluid during a cutting action. Depending upon the positioning of the saw teeth on the blade and the movement provided to the blade, one embodiment of the saw blade can be used for oscillatory cutting action and another embodiment of the saw blade can be used for reciprocating cutting action.

20 Claims, 3 Drawing Sheets

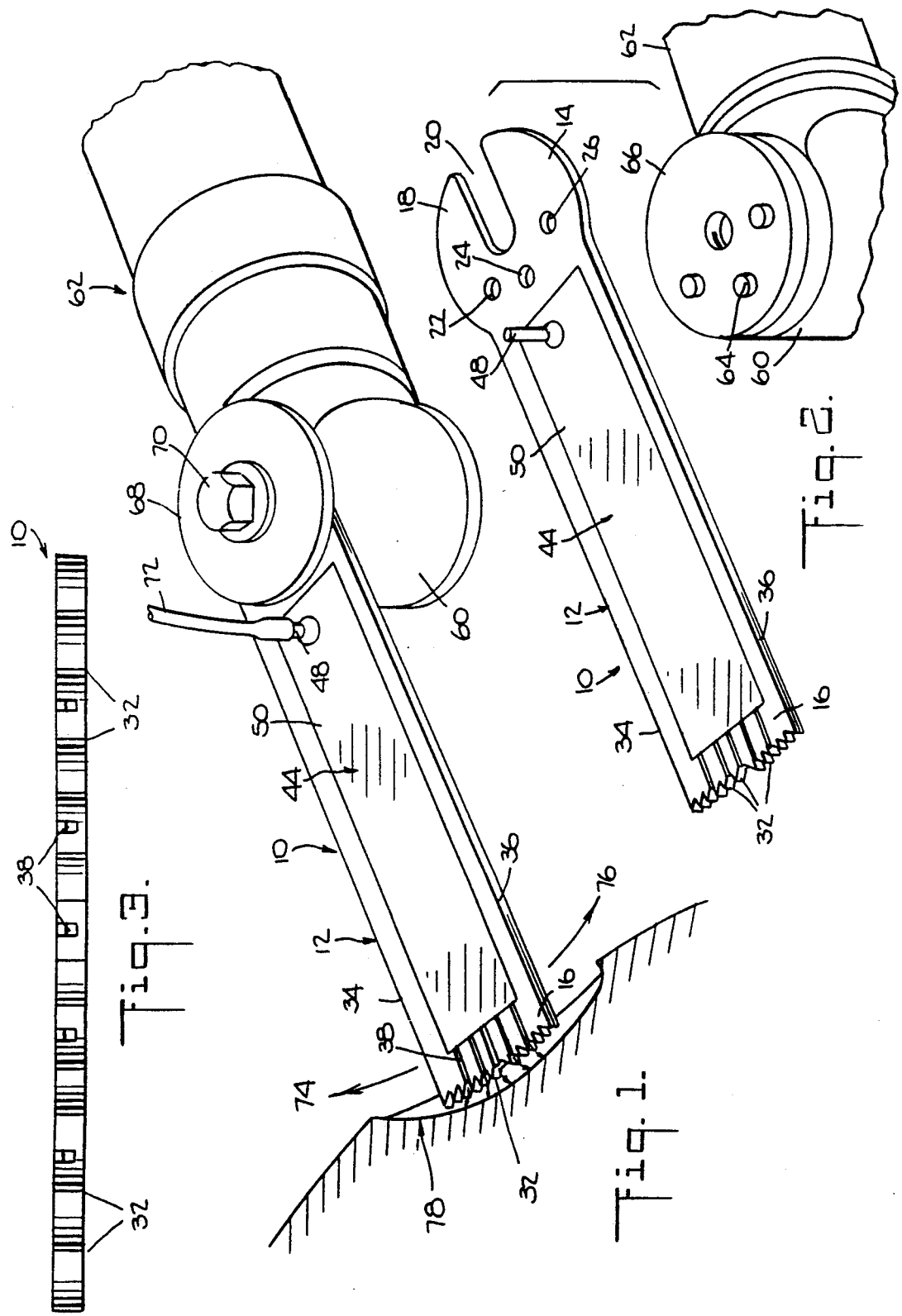

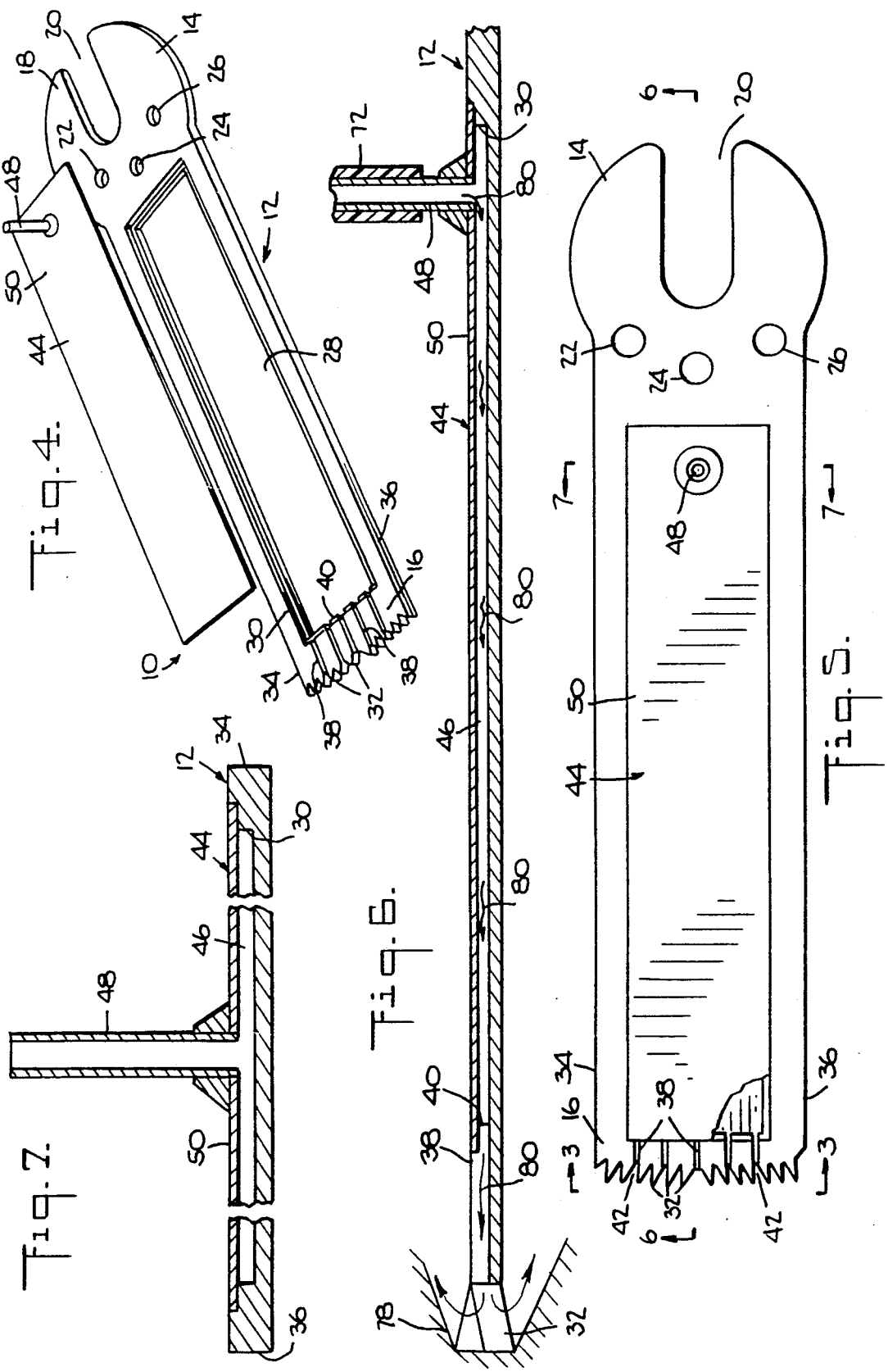

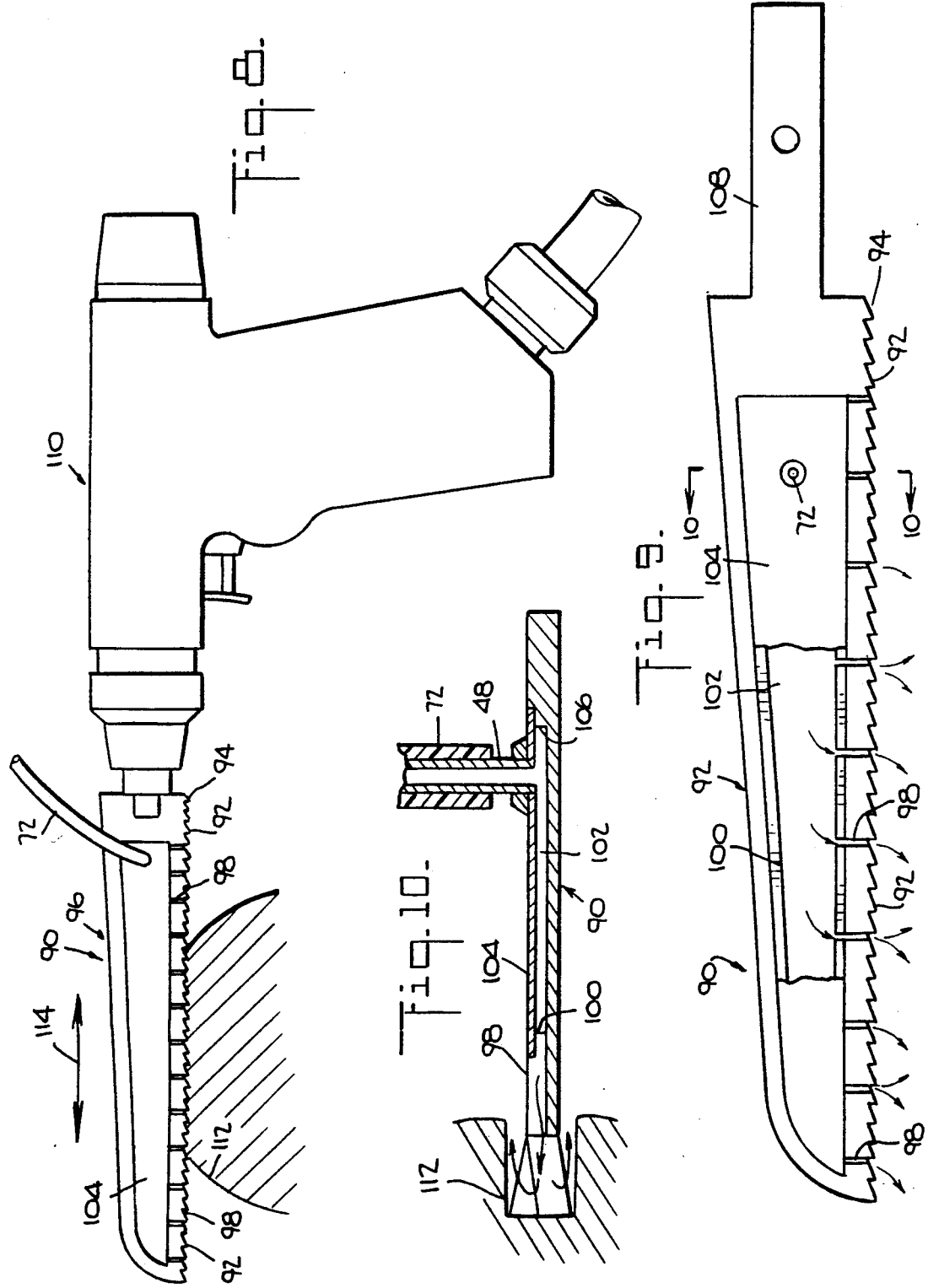

IRRIGATING SAW BLADE

BACKGROUND OF THE INVENTION

This invention relates to surgical cutting apparatus and methods for cutting tissue, and more particularly to a surgical saw blade that directs irrigating fluid at a cutting site while a cutting operation is being performed.

Saw blades for cutting tissue such as bone are well known and exemplified in U.S. Pat. Nos. 3,905,105; 3,905,374; 3,952,412; 4,513,742 and 4,584,999.

Generally, in any bone cutting operation there is a buildup of temperature at the cutting area or cutting site due to friction between the blade and the bone. If bone cutting temperatures increase beyond a predetermined level there is a possibility of bone necrosis, and a consequential prolongation of the healing process.

In some instances it is necessary to slow down the cutting procedure in order to control the buildup of cutting temperatures. However, such slowdowns, which result in extended operation times, can be discomforting to a patient and a strain on the surgeon.

The problem of heat buildup during a tissue cutting operation can be alleviated by dispersing fluid at the cutting site proximate the cutting blade. For example, U.S. Pat. No. 4,511,334 shows a dental cutting instrument for cutting slots into the jaw prior to installation of a dental prosthesis. The dental cutting instrument includes a circular saw blade having radial bores that extend from a hollow central drive shaft to the periphery of the blade, which contains cutting teeth. Coolant is introduced into the hollow drive shaft and dispersed through the radial bores of the blade to the cutting teeth.

In order for the dental cutting blade to adequately accommodate the bores, the blade is formed with radial thicknesses at the area of the bores. A blade of this type is relatively expensive to manufacture because the bores which conduct fluid from the hollow central drive shaft to the blade periphery must be precisely drilled. Of further concern is that the end of the bores which open at the cutting teeth are relatively small and are thus likely to become clogged by material removed during the cutting operation.

Another embodiment of U.S. Pat. No. 4,511,334 includes a cutting blade having radial slots formed in a face of the circular blade. A fluid hose accessory directs fluid into each of the slots sequentially as the blade rotates past the delivery end of the fluid hose, which is positioned slightly above the blade. Thus fluid is dispersed through only one slot at a time.

It is thus desirable to provide a surgical saw blade with an irrigation system that ensures uniform irrigation of a cutting site without clogging of the irrigation paths, and an irrigating saw blade that can be easily manufactured.

OBJECTS AND SUMMARY OF THE INVENTION

Among the several Objects of the invention may be noted the provision of a novel surgical saw blade, a novel surgical saw blade that directs irrigating fluid onto a cutting site, a novel surgical saw blade having independent irrigation channels fed from a common fluid filled manifold, a novel surgical saw blade, with irrigating capability, that is simple to construct, a novel surgical saw blade, with irrigating capability, that is relatively clog resistant, a novel surgical saw blade, with irrigating capability, that receives fluid in a manifold space within the saw blade and distributes fluid from the manifold space along separate irrigation channels, and a novel method for cutting tissue.

Other objects and features of the invention will be in part apparent and in part pointed out hereinafter.

The surgical saw blade, in accordance with one embodiment of the invention which provides an oscillatory cutting action, includes a main body portion and a cover portion joined to the main body portion such that the main body portion and the cover portion form an enclosed manifold space. Irrigation channels are formed in a face of the main body portion and extend from the manifold to saw teeth provided at an end portion of the saw blade.

In another embodiment of the saw blade, which can be used for reciprocatory cutting action, irrigation channels are provided along a longitudinal edge of the blade.

In either embodiment of the invention, the irrigation channels commonly communicate with the fluid manifold. The manifold receives fluid from a delivery hose that joins to a fluid inlet member provided at a proximal end of the cover plate.

In both embodiments of the invention, the fluid manifold is formed by providing a recess in the main body portion of the saw blade and covering the recess with a cover plate that is permanently joined to the main body portion of the saw blade.

Also, in both embodiments of the invention, the irrigation channels extend from a peripheral edge of the manifold to at least a root portion of the cutting teeth.

Since the irrigation channels are open from the manifold to the cutting teeth and the manifold is remote from the cutting teeth, there is little likelihood that the fluid flow from the manifold through the channels can become obstructed by cutting material removed by the cutting teeth.

The saw blade of each embodiment can be connected to respective surgical cutting instruments that provide the desired oscillatory and reciprocative blade cutting movement.

The invention accordingly comprises the constructions and methods hereinafter described, the scope of the invention being indicated in the claims.

DESCRIPTION OF THE DRAWINGS

In the accompanying drawings,

FIG. 1 is an enlarged fragmentary perspective view of a surgical cutting apparatus having a surgical saw blade incorporating one embodiment of the invention;

FIG. 2 is a view similar to FIG. 1 with the saw blade exploded from the cutting apparatus;

FIG. 3 is an end view thereof taken on the line 3—3 of FIG. 5;

FIG. 4 is an exploded perspective view of the saw blade;

FIG. 5 is a plan view thereof;

FIG. 6 is a sectional view taken on the line 6—6 of FIG. 5 showing the flow path of fluid through the saw blade;

FIG. 7 is a sectional view taken on the line 7—7 of FIG. 5;

FIG. 8 is a simplified schematic view of a surgical cutting apparatus having a saw blade incorporating another embodiment of the invention;

FIG. 9 is a plan view of the saw blade; and

FIG. 10 is a sectional view taken on the line 10—10 of FIG. 9.

Corresponding reference characters indicate corresponding parts throughout the several views of the drawings.

DETAILED DESCRIPTION OF THE INVENTION

A surgical saw blade incorporating one embodiment of the invention is generally indicated by the reference number 10 in FIGS. 1 and 2.

Referring to FIG. 4, the saw blade 10, which can be formed of any suitable material such as stainless steel, includes an elongated flat main body section 12, having a proximal end portion 14 and a distal end portion 16. The proximal end portion 14 is in the form of a generally circular mounting hub 18 having a longitudinal clearance recess 20 and three blade positioning openings 22, 24, and 26.

The main body portion 12 of the blade 10 further includes a generally rectangular elongated recess 28 (FIG. 4) intermediate the proximal and distal end portions 14 and 16. The recess 28 has a stepped peripheral edge portion 30 (FIG. 4).

The distal end portion 16 of the main body portion 12 is formed with a row of saw teeth 32 that runs from a longitudinal side edge 34 of the blade 10 to an opposite longitudinal side edge 36. A plurality of irrigation channels 38 extend longitudinally from a distal side 40 (FIG. 4) of the stepped peripheral edge portion 30 of the recess 28 (also referred to as the distal stepped peripheral edge 40). Preferably the respective irrigation channels 38 extend to at least to the respective root portions 42 of the saw teeth 32. The irrigation channels 38 are thus open from the distal stepped peripheral edge 40 to at least the root portions 42 of the saw teeth 32.

The saw blade 10 further includes a generally rectangular cover member 44, which can also be formed of stainless steel. The cover member 44 is sized to engage the stepped peripheral edge 30 of the recess 28 and be permanently joined thereto as by using a suitable bonding method such as welding or brazing, or any suitable known adhesive.

Thus, as clearly shown in FIGS. 6 and 7, the engagement of the cover member 44 with the stepped peripheral edge portion 30 of the main body portion 12 defines an enclosed manifold space 46 between the main body portion 12 and the cover member 44. As shown in FIG. 6, the cover member 44, while engaging the distal stepped peripheral edge 40, permits communication between the irrigation channels 38 and the manifold space 46.

A fluid inlet member 48 is joined to an outside surface 50 of the cover member 44 for communication with the manifold space 46. The fluid inlet member 48 can also be formed of any suitable material such as stainless steel and is welded or otherwise suitably joined to the cover member 44.

The precise dimensions of the saw blade 10 may vary based upon the particular cutting operation for which the blade is intended. Nevertheless, to exemplify the magnitudes being dealt with, the saw blade 10 can have an overall length between the proximal end 14 and the distal end 16 of approximately 3¾ inches, and a thickness of approximately 0.030 inches. The manifold space 46 can have a longitudinal extent of approximately 2.5 inches and a lateral extent of approximately 0.5 inches.

The thickness of the cover member 44 can be approximately 0.010 inches and the height of the enclosed manifold space 46 can be approximately 0.010 inches. The irrigation channels 38 can have a longitudinal extent of approximately 0.137 to 0.150 inches and a depth of approximately 0.020 inches.

Preparatory to using the saw blade 10, the proximal end portion 14 is engaged with a distal end portion 60 of a surgical cutting tool 62 such as a Hall oscillating saw, Model No. 5044-02, made by Hall Surgical, a Division of Zimmer.

The saw blade 10 is connected to the distal end 60 of the surgical tool 62 in a known manner such that one of the blade positioning openings 22, 24, 26 engages a positioning pin 64 on a mounting plate 66 of the surgical tool 62 to orient the saw blade 10 at a predetermined angle relative to the tool 62. The proximal end 14 of the saw blade 10 is clamped to the mounting plate 66 by a hold down plate 68 and a bolt 70.

A hose member 72 (FIG. 1) is interconnected at one end with the saw blade 10 at the fluid inlet member 48 and joined at an opposite end (not shown) to a fluid supply source (not shown) which pumps a suitable fluid such as saline through the hose member 72 at a predetermined rate.

In using the saw blade 10, the surgical tool 62 drives the saw blade along an oscillatory path in the direction shown by the arrows 74 and 76 in FIG. 1 to cut tissue at the surgical site 78. During oscillatory action of the saw blade 10, fluid is fed through the hose member 72 and the inlet member 48 in the direction of the arrows 80, as shown in FIG. 6, for passage into the manifold space 46. The fluid entering the manifold space 46 is expelled via the irrigation channels 38 for dispersal past the saw teeth 32 at the cutting site 78.

As the cutting action of the saw teeth 32 removes bone tissue from the surgical cutting site 78, fluid that flows through the irrigation channels 38 toward the saw teeth 32 helps flush away the cut material and cool the uncut tissue at the cutting site 78. Since the fluid entering the irrigation channels 38 at the distal stepped peripheral edge 40 (FIG. 6) is relatively remote from the contact area between the saw teeth 32 and the bone tissue at the cutting site 78, as shown in FIG. 6, the possibility that the cut material 74 will clog the irrigation channels 38 at their source is minimal. The open nature of the channels 38 also minimizes the likelihood of clogged channels. Consequently a uniform flow of fluid from the irrigation channels 38 toward the cutting site 78 is substantially assured and the problem of bone necrosis that can occur at high temperature bone cutting is substantially reduced.

The fluid that is pumped through the manifold space 46 into the irrigation channels 38 for dispersal at the saw teeth 32 during bone cutting or bone resection, also permits improved debridement of the resection area.

It will be noted that the fluid inlet member 48 is positioned near the proximal end 14 of the cutting blade 10 so as to avoid interfering with the oscillatory cutting action of the blade at the distal end 16. The irrigation fluid is pumped by any well known irrigation system (not shown).

Another embodiment of the saw blade is generally indicated by the reference number 90 in FIG. 8. The saw blade 90 differs from the saw blade 10 by provision of cutting teeth 92 at a longitudinal edge 94 of a main body portion 96 of the saw blade 90 for reciprocal cutting in the longitudinal direction indicated by the arrows 114 in FIG. 8. A plurality of irrigation channels 98, similar to the irrigation channels 38, extend from a longitudinal peripheral stepped edge portion 100 of an enclosed manifold 102 of the saw blade 90. The manifold 102 is similar to the manifold 46 of the saw blade 10, in that it is defined by engagement of a cover plate 104 with the stepped peripheral edge portion 100 of a manifold recess 106 in a manner similar to that previously described for the manifold 46. The saw blade 90 also includes a proximal mounting portion 108.

In using the saw blade 90, a surgical cutting apparatus 110 onto which the blade 90 is mounted in a suitable known manner provides the blade 90 with a reciprocatory cutting action. Fluid is pumped through the hose 72 to the manifold 102 for egress through the irrigation channels 98 at the area of the saw teeth 92. Dispersion of fluid at the saw teeth 92 as the teeth engage bone at a cutting site 112 allows for improved debridement of the resection area during bone resection.

The flow of fluid through the irrigation channels 98 of the saw blade 90 also reduces cutting temperatures which consequentially reduces the potential for bone necrosis in the manner previously described for the saw blade 10. By reducing the possibility of bone necrosis, trauma and discomfort to the patient is reduced and the healing process improved.

Some advantages of the invention evident from the foregoing description include an irrigating saw blade which allows dispersion of irrigation fluid at the cutting teeth of a cutting blade. The cutting blade can be an oscillating saw blade or a reciprocating saw blade. The body of the blade need not be locally thickened to permit formation of the irrigation channel and such irrigation channels can be formed in blades that use standard blade guide templates. The irrigation dispersion channels allow delivery of fluid at the root of the saw teeth as well as beyond the teeth to provide a self flushing action that reduces the possibility of irrigation channel obstruction. A further advantage is that the saw blade is relatively economical to manufacture since it does not require precision drilling or specially shaped blade members that are thickened at the irrigation flow path.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A surgical saw blade for use in tissue cutting comprising,
   a. a main body portion and a cover portion joined to said main body portion, said main body portion and said cover portion being formed to define an enclosed manifold space between said main body portion and said cover portion,
   b. fluid inlet means on one of said portions to convey fluid into said manifold space,
   c. cutting means formed on one of said portions for cutting engagement with said tissue, and
   d. a plurality of fluid channels communicable with said manifold space and extending from said manifold space to said cutting means.

2. A surgical saw blade as claimed in claim 1 wherein said main body portion is formed with a recess and said cover portion is formed to cover and enclose said recess to define the manifold space between said cover portion and said main body portion.

3. A surgical saw blade as claimed in claim 1 wherein said fluid inlet means is formed on said cover portion.

4. A surgical saw blade as claimed in claim 1 wherein said cutting means is formed on said main body portion.

5. A surgical saw blade as claimed in claim 4 wherein said main body portion has a distal end, and said cutting means include cutting teeth formed on said distal end.

6. A surgical saw blade as claimed in claim 5 wherein said manifold has a distal end corresponding to the distal end of the main body portion and said fluid channels extend from said distal end of said manifold to said cutting teeth.

7. A surgical saw blade as claimed in claim 4 wherein said main body portion has oppositely disposed proximal and distal ends and a longitudinal side edge intermediate said proximal and distal ends, and said cutting means include cutting teeth formed on said longitudinal side edge.

8. A surgical saw blade as claimed in claim 7 wherein said manifold has proximal and distal ends corresponding to the proximal and distal ends of the main body portion and a longitudinal side edge corresponding to the longitudinal side edge of said main body portion and said fluid channels extend from the longitudinal side edge of said manifold to the cutting teeth at the longitudinal side edge of said main body portion.

9. A surgical saw blade as claimed in claim 4 wherein said fluid channels are formed in said main body portion.

10. A surgical saw blade as claimed in claim 1 wherein said main body portion is formed with a recess and said cover portion is formed to cover and enclose said recess, said fluid channels being formed in said main body portion to direct fluid from said manifold space to said cutting means.

11. A surgical saw blade as claimed in claim 10 wherein said recess includes a stepped peripheral edge portion and said cover portion is sized to engage said stepped peripheral edge portion.

12. A surgical saw blade as claimed in claim 10 wherein said main body portion is substantially flat and said cover portion is substantially coplanar with said main body portion.

13. A surgical saw blade for use in tissue cutting comprising,
   a. a main body portion having a proximal end and a distal end, said distal end being formed with saw teeth, said proximal end being formed with means for driving engagement with a drive means that moves said saw blade on an oscillatory path,
   b. said main body portion including an elongated recess, cover means for covering said recess to define an enclosed manifold space between said main body portion and said cover portion,
   c. fluid inlet means on said cover means for conveying fluid into said manifold space, and
   d. a plurality of fluid channels communicable with said manifold space and extending from said manifold space to said saw teeth.

14. A surgical saw blade as claimed in claim 13 wherein said fluid channels are in the form of slits and said manifold has a proximal end portion and a distal end portion, said slits extending from the distal end portion of said manifold to said saw teeth.

15. A surgical saw blade as claimed in claim 14 wherein said slits are separate from each other and commonly communicable with said manifold space.

16. A surgical saw blade for use in tissue cutting comprising,
   a. a main body portion having a proximal end and a distal end, and a longitudinal side edge intermediate said proximal and distal ends, said longitudinal side edge being formed with saw teeth, said proximal end being formed with means for driving engagement with a drive means that moves said saw blade on a reciprocatory path,
   b. said main body portion including an elongated recess, cover means for covering said recess to define an enclosed manifold space between said main body portion and said cover portion,
   c. fluid inlet means on said cover means for conveying fluid into said manifold space, and
   d. a plurality of fluid channels communicable with said manifold space and extending from said manifold space to said saw teeth.

17. A surgical saw blade as claimed in claim 16 wherein said fluid channels are in the form of slits and said manifold has a proximal end portion and a distal end portion, said slits being provided between said proximal end portion and the distal end portion of said manifold and extending from said manifold to said saw teeth.

18. A surgical saw blade as claimed in claim 17 wherein said slits are separate from each other and commonly communicable with said manifold space.

19. A method of cutting tissue comprising,
   a. providing a blade with a cutting edge and forming a plurality of irrigation channels in the face of the blade such that the irrigation channels are directed into the cutting edge,
   b. forming a manifold in the blade to commonly communicate with each of the irrigation channels by joining a cover piece to the blade to define an enclosed manifold space between the cover piece and the blade,
   c. causing said blade to reciprocate and engaging said cutting edge with tissue in a cutting action,
   d. directing fluid into the manifold for movement through the manifold for dispersion from the manifold through the irrigation channels whereby a cutting action of the blade at the cutting edge is accompanied by dispersion of fluid through the irrigation channels to cool and lubricate the cutting action.

20. The method as claimed in claim 19 wherein the step of forming a manifold includes the formation of a recess in the blade and, covering and enclosing the recess with the cover piece to form the enclosed manifold space.

* * * * *